United States Patent [19]

Tazuma et al.

[11] 4,143,045
[45] Mar. 6, 1979

[54] METHOD OF PREPARING DIBENZOTHIAZOLYL DISULFIDES

[75] Inventors: James J. Tazuma, Stow; Angelo Bergomi, Akron, both of Ohio

[73] Assignee: The Goodyear Tire & Rubber Company, Akron, Ohio

[21] Appl. No.: 852,400

[22] Filed: Nov. 17, 1977

Related U.S. Application Data

[63] Continuation of Ser. No. 637,243, Dec. 3, 1975, abandoned, which is a continuation of Ser. No. 504,018, Sep. 9, 1974, abandoned, which is a continuation of Ser. No. 301,691, Oct. 27, 1972, abandoned.

[51] Int. Cl.$^2$ ........................................... C07D 277/78
[52] U.S. Cl. ................................................. 260/306.5
[58] Field of Search ..................................... 260/306.5

[56] References Cited

U.S. PATENT DOCUMENTS

| 2,024,567 | 12/1935 | Clifford | 260/16 |
| 2,593,761 | 4/1952 | Johnstone | 196/29 |
| 3,925,401 | 12/1975 | Janin | 260/306.5 |

FOREIGN PATENT DOCUMENTS 2349314  10/1972  Fed. Rep. of Germany.

OTHER PUBLICATIONS

Field et al., JACS, vol. 80, 838, 841(1958).
Osttenberg, Cancer Research 28, 2539–2541(1968).

*Primary Examiner*—Nicholas S. Rizzo
*Attorney, Agent, or Firm*—H. C. Young, Jr.

[57] ABSTRACT

Method of preparing dibenzothiazolyl disulfides by oxidizing mercaptobenzothiazole in a substantially neutral saturated aliphatic alcohol solution with a hydroperoxide. The invention has particular utility by providing a relatively pollution-free method of preparing dibenzothiazolyl disulfides.

1 Claim, No Drawings

METHOD OF PREPARING DIBENZOTHIAZOLYL DISULFIDES

This is a continuation of application Ser. No. 637,243 filed Dec. 3, 1975, now abandoned, which was a continuation of application Ser. No. 504,018, filed Sept. 9, 1974, now abandoned, which was a continuation of application Ser. No. 301,691, filed Oct. 27, 1972, now abandoned.

This invention relates to a method of preparing dibenzothiazolyl disulfide.

Dibenzothiazolyl disulfide has typically been prepared by dissolving mercaptobenzothiazole in aqueous alkali and oxidizing the resulting salt with a suitable oxidant.

Various oxidizing agents have been proposed. They typically consist of a combination of an oxidant with a strong mineral acid, such as sodium nitrite and sulfuric acid. It has also been proposed to oxidize the Na salt of mercaptobenzothiazole in a neutral or alkaline medium with halogens or ammonium persulfate. In each of these systems, however, the inorganic byproducts resulting from the reaction, such as the inorganic salt produced by neutralizing the mineral acid, must be especially treated or be discharged as environmental pollutants.

It is, therefore, an object of this invention to provide a relatively pollution-free process for the preparation of dibenzothiazolyl disulfide.

In accordance with this invention, it has been discovered that a method of preparing dibenzothiazolyl disulfide comprises oxidizing mercaptobenzothiazole in a solution of a saturated aliphatic alcohol having 1 to 4 carbon atoms with a hydroperoxide selected from hydrogen peroxide, alkyl hydroperoxides and aralkyl hydroperoxides, where said alcohol solution has a substantially autogeneous acid-base condition.

It is an important unexpected result of this invention that the reaction of the peroxide with the mercaptobenzothiazole in the alcohol solution, without the aid of a strong mineral acid, efficiently produces the dibenzothiazolyl disulfide in a relatively high purity form, typically with a yield of at least about 98 percent, and usually with a practically quantitative yield. As example of the unusual purity of the product obtained without further purification steps such as crystallization, the dibenzothiazolyl disulfide typically has a melting point of about 180° C., according to standard capillary tube determination with a heating rate of about 1° C. per minute.

In the practice of this invention, although it is preferred to start the reaction with a 100 percent alcohol solution, a minor amount of water can be present with the desired surprising results still being obtained. Thus, the starting alcohol solution can comprise from about 100 to 80 weight percent alcohol and, correspondingly, about zero up to about 20 weight percent water.

It is a further important primary advantage of this invention that the primary byproducts are water and alcohol, instead of the inorganic salt byproducts normally produced with the indicated other typical oxidizing systems.

A mole ratio of peroxide to mercaptobenzothiazole of 0.5:1 is required by the stoichiometry of the reaction. A range of about 0.3:1 to about 0.7:1 is usually acceptable. A smaller ratio can result in insufficient oxidation and a larger ratio can result in over-oxidation.

Usually, a weight ratio of alcohol or alcohol-water mixture to mercaptobenzothiazole of about 30:1 to about 3:1, preferably about 20:1 to about 5:1, is used, depending primarily on the desired thickness or viscosity of the mixture.

Usually, a satisfactory temperature for the relatively fast oxidation reaction is in the range of about 0° C. to about 100° C., preferably about 30° C. to about 80° C., but not appreciably above the boiling point of the alcohol solution. The reaction can be conducted in bulk or on a continuous basis at atmospheric pressure or above or below atmospheric pressure. Usually the autogenous pressure of the mixture is satisfactory. The oxidation is typically fast and efficient without the addition of a strong mineral acid with essentially the only byproducts being water and alcohol. The dibenzothiazolyl disulfide is then simply recovered as a high purity solid product by conventional means such as by filtration.

In the practice of this invention, it is preferred that the alcohol solution be substantially neutral with its condition being the acidity or basicity autogeneously developed by the reactants.

Various liquid alcohols can be used as the reaction medium of this invention such as saturated aliphatic alcohols having B 1 to 4 carbon atoms representative of which are methyl alcohol, ethyl alcohol, isopropyl alcohol and t-butyl alcohol. Methyl alcohol and isopropyl alcohol are preferred.

Various hydroperoxides can be used in the mercaptobenzothiazole oxidation step of this invention. Representative of the various hydroperoxides are hydrogen peroxide, alkyl hydroperoxides and aralkyl hydroperoxides. The alkyl radicals of the hydroperoxides are saturated aliphatic radicals having 3 to 6 carbon atoms such as n-propyl, i-propyl, n-butyl, i-butyl, t-butyl, n-pentyl, i-pentyl, t-pentyl, n-hexyl, i-hexyl and t-hexyl radicals. Thus, representative of the alkyl hydroperoxides are t-butyl and t-amyl hydroperoxides and representative of the aralkyl hydroperoxides are cumene, ethyltoluene, ethylchlorobenzene and ethyl(t-butylbenzene) hydroperoxides. Hydrogen peroxide is preferred.

In the further practice of this invention, a method is provided for producing valuable compounds as monomers which comprises dehydrating by conventional means the alcohols produced in the oxidation step of this invention. Thus, when the various hydroperoxides are used, the corresponding alcohols obtained during the oxidation step of the mercaptobenzothiazole can be dehydrated to the corresponding vinyl derivative. These products are valuable monomeric materials. For example, dimethylphenyl carbinol, methyltolyl carbinol, methylchlorophenyl carbinol and methyl(t-butylphenyl) carbinol can be obtained from cumene hydroperoxide, ethyltoluene hydroperoxide, ethylchlorobenzene hydroperoxide and ethyl (t-butylbenzene) hydroperoxide, respectively, which can, in turn, be dehydrated by conventional dehydration procedure to the corresponding compounds such as alpha methyl styrene, vinyltoluene, vinylchlorobenzene and vinyl(t-butylbenzene), respectively.

The practice of this invention is further illustrated by reference to the following example which is intended to be representative rather than restrictive of the scope of the invention. Unless otherwise indicated, all parts and percentages are by weight.

EXAMPLE I

To a reactor fitted with a stirrer, condenser and addition funnel was charged 20 parts of mercaptobenzothiazole (MBT) and 160 parts of methanol. The mixture was heated and refluxed at atmospheric pressure until the MBT dissolved. To the solution was then mixed, by adding dropwise, 46.8 parts of a methanol solution of 30 weight percent hydrogen peroxide which had been prepared by dissolving 6.8 parts of 30 weight percent hydrogen peroxide in 40 parts methanol while stirring the mixture at reflux. After the addition, the resultant mixture was stirred for an additional 20 minutes. The mixture was then allowed to cool to about 20° C. and was filtered. The dibenzothiazolyl disulfide produced was dried under vacuum at 40° C. and its melting point determined to be 180° C. The melting point was determined with a capillary tube with a heating rate of 1° C. per minute. In the conduct of the reaction, only water was formed as a byproduct instead of the typical organic impurity precipitates mixed with the disulfide which typically occur during the oxidation of the sodium salt of the mercaptobenzothiazole in an aqueous solution.

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing dibenzothiazolyl disulfide having a melting point of about 180° C. as determined with a capillary tube with a heating rate of about 1° C. per minute, in a yield of at least about 98 percent without the aid of a mineral acid where the byproducts are water and dimethylphenylcarbinol instead of inorganic salt byproducts, which method consists of oxidizing mercaptobenzothiazole in a solution of alcohol selected from at least one of methyl alcohol and isopropyl alcohol at a temperature in the range of about 30° C. to about 80° C., but not above the boiling point of said alcohol solution, by reacting cumene hydroperoxide therewith; where said alcohol solution has an autogenous acid-base condition developed by the reaction system itself, where said alcohol solution comprises from 100 to about 80 weight percent of said alcohol and correspondingly up to about 20 weight percent water, and where the mole ratio of said cumene hydroperoxide to said mercaptobenzothiazole is in the range of about 0.3:1 to about 0.7:1.

* * * * *